United States Patent
Martin et al.

(10) Patent No.: US 6,206,849 B1
(45) Date of Patent: *Mar. 27, 2001

(54) MULTIPLE LUMEN CATHETER

(75) Inventors: Geoffrey S. Martin; Michael R. Leblanc, both of Mississauga (CA)

(73) Assignee: Vas-Cath Incorporated, Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/139,705

(22) Filed: Aug. 25, 1998

(Under 37 CFR 1.47)

Related U.S. Application Data

(63) Continuation of application No. 08/481,169, filed on Jun. 7, 1995, now Pat. No. 5,797,869, which is a continuation of application No. 08/205,331, filed on Mar. 3, 1994, now Pat. No. 5,472,417, which is a continuation of application No. 07/785,351, filed on Oct. 30, 1991, now abandoned, which is a continuation of application No. 07/288,364, filed on Dec. 27, 1988, now Pat. No. 5,195,962.

(30) Foreign Application Priority Data

Dec. 22, 1987 (CA) ................................ 555076

(51) Int. Cl.$^7$ ................................ A63M 3/00
(52) U.S. Cl. ................ 604/43; 604/264; 604/523
(58) Field of Search .............. 138/111–117; 604/4–7, 604/43, 164–169, 264, 523, 524

(56) References Cited

U.S. PATENT DOCUMENTS

| Re. 31,873 | 4/1985 | Howes . |
|---|---|---|
| D. 272,651 | 2/1984 | Mahurkar . |
| 550,238 | 11/1895 | Allen, Jr. . |
| 1,696,018 | 12/1928 | Schellberg . |
| 1,922,084 | 8/1933 | Gerow . |

(List continued on next page.)

FOREIGN PATENT DOCUMENTS

| 0834211 | 2/1976 | (BE) . |
|---|---|---|
| 0960932 | 1/1975 | (CA) . |
| 1092927 | 1/1981 | (CA) . |

(List continued on next page.)

OTHER PUBLICATIONS

Stephen P. Gatt, *A Quadruple–Lumen Intravenous Infusion Catheter*, 11 Anaesth Intens Care 261–62 (1983).

Arrow International, Inc., *510(k) Notification for Multi–Lumen M.I.S.™ Catheterization System* (Apr. 14, 1982).

Arrow International, Inc., *510(k) Notification for Arrow Central Venous Multi–Lumen Catheter with Flex Tip* (Aug. 25, 1986).

(List continued on next page.)

*Primary Examiner*—Ronald K. Stright, Jr.
(74) *Attorney, Agent, or Firm*—Trask Britt

(57) ABSTRACT

The invention provides a cylindrical elongate body extending from a proximal to a distal end, the body defining two similar longitudinally extending lumens separated by a septum and a further lumen defined within the septum, a tip extending from the distal end of the body defining a part of the further lumen, a connector at the proximal end, tubes coupled to the connector and in fluid communication through the connector one with each of the respective lumens, the body defining openings providing access one to each of the longitudinally extending lumens, the openings being spaced from one another longitudinally of the body and the further lumen extending longitudinally beyond the longitudinally extending lumens and through the tip, the further lumen terminating at an opening at the distal end of the tip and the tip being convergently tapered as it extends longitudinally from the body and the longitudinally extending lumens being blocked immediately adjacent and distally of the openings.

18 Claims, 9 Drawing Sheets

U.S. PATENT DOCUMENTS

| | | |
|---|---|---|
| 2,173,527 | 9/1939 | Agayoff . |
| 2,175,726 | 10/1939 | Gebauer . |
| 2,230,218 | 2/1941 | Asche . |
| 2,409,343 | 10/1946 | Curtis . |
| 2,473,742 | 6/1949 | Auzin . |
| 2,561,569 | 7/1951 | Flynn . |
| 2,564,977 | 8/1951 | Hu . |
| 2,590,895 | 4/1952 | Scarpellino . |
| 2,819,718 | 1/1958 | Goldman . |
| 2,936,761 | 5/1960 | Snyder . |
| 3,042,045 | 7/1962 | Sheridan . |
| 3,055,361 | 9/1962 | Ballard . |
| 3,064,653 | 11/1962 | Coanda . |
| 3,174,890 | 3/1965 | Goyke . |
| 3,322,590 | 5/1967 | Clark . |
| 3,324,854 | 6/1967 | Weese . |
| 3,331,371 | 7/1967 | Rochi et al. . |
| 3,359,974 | 12/1967 | Khalil . |
| 3,370,587 | 2/1968 | Vizcarra . |
| 3,394,705 | 7/1968 | Abramson . |
| 3,411,506 | 11/1968 | Velasco . |
| 3,437,088 | 4/1969 | Bielinski . |
| 3,448,739 | 6/1969 | Stark et al. . |
| 3,452,756 | 7/1969 | Harautuneian . |
| 3,467,180 | 9/1969 | Pensotti . |
| 3,469,579 | 9/1969 | Hubert . |
| 3,528,869 | 9/1970 | Derenuik ............... 156/294 |
| 3,593,713 | 7/1971 | Bogoff et al. . |
| 3,625,793 | 12/1971 | Sheridan et al. . |
| 3,634,924 | 1/1972 | Blake et al. . |
| 3,720,210 | 3/1973 | Diettrich . |
| 3,726,281 | 4/1973 | Norton et al. . |
| 3,746,003 | 7/1973 | Blake et al. . |
| 3,746,033 | 7/1973 | Keiper, II . |
| 3,771,527 | 11/1973 | Ruisi . |
| 3,804,097 | 4/1974 | Rudie . |
| 3,805,794 * | 4/1974 | Schlesinger . |
| 3,817,389 | 6/1974 | Weichselbaum . |
| 3,848,602 | 11/1974 | Gutnick . |
| 3,885,567 | 5/1975 | Ross . |
| 3,888,249 | 6/1975 | Spencer . |
| 3,976,529 | 8/1976 | Weichselbaum . |
| 3,983,203 | 9/1976 | Corbett . |
| 3,995,623 | 12/1976 | Blake et al. . |
| 4,003,665 | 1/1977 | Dreyer et al. . |
| 4,004,588 | 1/1977 | Alexander . |
| 4,016,879 | 4/1977 | Mellor . |
| 4,027,668 | 6/1977 | Dunn . |
| 4,037,599 | 7/1977 | Raulerson . |
| 4,050,667 | 9/1977 | Kossett . |
| 4,057,065 | 11/1977 | Thow . |
| 4,063,980 | 12/1977 | Trunnell . |
| 4,072,146 * | 2/1978 | Howes . |
| 4,072,153 | 2/1978 | Swartz . |
| 4,098,275 | 7/1978 | Consalvo . |
| 4,099,528 | 7/1978 | Sorenson et al. . |
| 4,100,246 | 7/1978 | Frisch . |
| 4,134,402 * | 1/1979 | Mahurkar . |
| 4,168,703 | 9/1979 | Kenigsberg ............... 604/280 |
| 4,171,943 | 10/1979 | Tschanz et al. . |
| 4,178,936 | 12/1979 | Newcomb . |
| 4,180,068 | 12/1979 | Jacobsen et al. . |
| 4,180,076 | 12/1979 | Betancourt . |
| 4,198,984 | 4/1980 | Taylor . |
| 4,202,332 | 5/1980 | Tersteegen et al. . |
| 4,203,436 | 5/1980 | Grimsrud . |
| 4,210,479 | 7/1980 | Fabisiewicz . |
| 4,214,593 | 7/1980 | Imbruce et al. . |
| 4,217,895 | 8/1980 | Sagae et al. . |
| 4,248,224 | 2/1981 | Jones . |
| 4,251,305 | 2/1981 | Becker et al. ............... 604/103 |
| 4,268,338 | 5/1981 | Peterson . |
| 4,270,535 | 6/1981 | Bogue et al. . |
| 4,299,226 | 11/1981 | Banka . |
| 4,309,994 | 1/1982 | Grunwald . |
| 4,336,036 | 6/1982 | Leeke et al. . |
| 4,352,354 | 10/1982 | Ujihara . |
| 4,354,495 | 10/1982 | Bodicky . |
| 4,364,394 | 12/1982 | Wilkinson . |
| 4,384,186 | 5/1983 | Burt . |
| 4,385,631 | 5/1983 | Uthmann . |
| 4,390,383 | 6/1983 | Van Dongeren ............... 156/294 |
| 4,392,848 | 7/1983 | Lucas et al. . |
| 4,398,910 | 8/1983 | Blake et al. . |
| 4,403,983 | 9/1983 | Edelman et al. . |
| 4,403,985 | 9/1983 | Boretos ............... 604/53 |
| 4,404,159 | 9/1983 | McFarlane ............... 264/296 |
| 4,405,313 | 9/1983 | Sisley et al. ............... 604/43 |
| 4,406,656 | 9/1983 | Hattler et al. ............... 604/280 |
| 4,419,095 | 12/1983 | Nebergall et al. ............... 604/96 |
| 4,425,177 | 1/1984 | Shinno . |
| 4,451,252 | 5/1984 | Martin . |
| 4,484,585 | 11/1984 | Baier . |
| 4,493,696 | 1/1985 | Uldall ............... 604/43 |
| 4,496,353 | 1/1985 | Overland et al. ............... 604/272 |
| 4,543,057 * | 9/1985 | Sommercorn et al. . |
| 4,543,087 | 9/1985 | Sommercom et al. ............... 604/43 |
| 4,545,390 | 10/1985 | Leary . |
| 4,551,292 | 11/1985 | Fletcher et al. ............... 264/139 |
| 4,568,329 | 2/1986 | Mahurkar ............... 604/43 |
| 4,573,966 | 3/1986 | Weikl et al. ............... 604/53 |
| 4,583,968 | 4/1986 | Mahurkar ............... 604/280 |
| 4,619,643 | 10/1986 | Bai ............... 604/43 |
| 4,623,327 | 11/1986 | Mahurkar ............... 604/4 |
| 4,643,711 | 2/1987 | Bates ............... 604/4 |
| 4,661,300 | 4/1987 | Daugherty ............... 264/40.6 |
| 4,668,221 * | 5/1987 | Luther ............... 604/168 |
| 4,668,225 | 5/1987 | Russo et al. ............... 604/280 |
| 4,670,009 | 6/1987 | Bullock ............... 604/280 |
| 4,681,564 | 7/1987 | Landreneau ............... 604/280 |
| 4,682,978 | 7/1987 | Martin ............... 604/43 |
| 4,692,141 | 9/1987 | Mahurkar ............... 604/43 |
| 4,701,159 | 10/1987 | Brown et al. ............... 604/43 |
| 4,714,460 | 12/1987 | Calderon ............... 604/28 |
| 4,717,379 | 1/1988 | Ekholmer ............... 604/43 |
| 4,748,984 | 6/1988 | Patel . |
| 4,753,640 | 6/1988 | Nichols et al. ............... 604/247 |
| 4,756,303 | 7/1988 | Kawashima et al. . |
| 4,762,120 | 8/1988 | Hussein . |
| 4,763,654 | 8/1988 | Jang . |
| 4,769,005 | 9/1988 | Ginsburg et al. ............... 604/164 |
| 4,772,268 * | 9/1988 | Bates ............... 604/43 |
| 4,782,834 | 11/1988 | Maguire et al. . |
| 4,790,813 | 12/1988 | Kensey ............... 604/22 |
| 4,795,439 | 1/1989 | Guest ............... 604/43 |
| 4,801,297 | 1/1989 | Mueller ............... 604/280 |
| 4,813,429 | 3/1989 | Eshel et al. ............... 604/43 |
| 4,822,345 * | 4/1989 | Danforth . |
| 4,838,881 | 6/1989 | Bennett ............... 604/280 |
| 4,842,582 | 6/1989 | Mahurkar ............... 604/43 |
| 4,867,742 | 9/1989 | Calderon ............... 604/28 |
| 4,894,057 | 1/1990 | Howes ............... 604/280 |
| 4,898,591 | 2/1990 | Jang et al. ............... 604/282 |
| 4,934,340 | 6/1990 | Ebling et al. . |
| 4,961,809 | 10/1990 | Martin ............... 604/280 |
| 4,968,307 | 11/1990 | Dake et al. ............... 604/280 |
| 4,995,865 | 2/1991 | Gahara et al. ............... 604/43 |
| 5,004,455 | 4/1991 | Greenwood et al. ............... 604/43 |
| 5,007,897 | 4/1991 | Kalb et al. ............... 604/43 |
| 5,009,636 | 4/1991 | Wortley et al. ............... 604/43 |
| 5,015,232 | 5/1991 | Maglinte ............... 604/96 |

| | | |
|---|---|---|
| 5,019,057 | 5/1991 | Truckai .............................. 604/282 |
| 5,021,044 | 6/1991 | Sharkawy .............................. 604/53 |
| 5,057,073 | 10/1991 | Martin .................................. 604/43 |
| 5,135,599 * | 8/1992 | Martin et al. ......................... 604/523 |
| 5,167,623 | 12/1992 | Cianci et al. ........................... 604/43 |
| 5,195,962 * | 3/1993 | Martin et al. ........................... 604/43 |
| 5,207,650 | 5/1993 | Martin .................................. 604/173 |
| 5,221,255 | 6/1993 | Mahurkar et al. ..................... 604/43 |
| 5,221,256 | 6/1993 | Mahurkar .............................. 604/43 |
| 5,236,417 * | 8/1993 | Wallis .................................. 604/164 |
| 5,451,206 | 9/1995 | Young .................................... 604/43 |
| 5,472,417 * | 12/1995 | Martin et al. ........................... 604/43 |
| 5,797,869 * | 8/1998 | Martin et al. ......................... 604/523 |

FOREIGN PATENT DOCUMENTS

| | | |
|---|---|---|
| 1112533 | 11/1981 | (CA) . |
| 0050089 | 8/1982 | (CA) . |
| 1150122 | 7/1983 | (CA) . |
| 1167727 | 5/1984 | (CA) . |
| 0195412 | 5/1907 | (DE) . |
| 2447804 A1 | 10/1974 | (DE) . |
| 19 346 | 4/1982 | (DE) . |
| 3130454 C2 | 4/1985 | (DE) . |
| 3506738 A1 | 11/1985 | (DE) . |
| 3112762 C2 | 6/1988 | (DE) . |
| 0036642 A2 | 9/1981 | (EP) . |
| 0079719 A1 | 5/1983 | (EP) . |
| 0025704 B1 | 10/1983 | (EP) . |
| 0322225 A2 | 12/1988 | (EP) . |
| 0333308 A2 | 9/1989 | (EP) . |
| 0161863 B1 | 7/1990 | (EP) . |
| 0440992 A2 | 12/1990 | (EP) . |
| 0555780 A2 | 2/1993 | (EP) . |
| 0381062 B1 | 3/1994 | (EP) . |
| 0804309 | 10/1936 | (FR) . |
| 1285953 | 1/1962 | (FR) . |
| 1508959 | 1/1962 | (FR) . |
| 2201908 | 10/1972 | (FR) . |
| 2201908 | 5/1974 | (FR) . |
| 2285148 | 9/1974 | (FR) . |
| 2297640 | 1/1975 | (FR) . |
| 2530958 | 7/1982 | (FR) . |
| 2513520 | 4/1983 | (FR) . |
| 2565491 | 6/1984 | (FR) . |
| 1419702 | 12/1975 | (GB) . |
| 2043449 | 10/1980 | (GB) . |
| 54-34587 | 8/1977 | (JP) . |
| 55-40512 | 9/1978 | (JP) . |

OTHER PUBLICATIONS

Arrow International, Inc., *Arrow®–Howes™ Multi–Lumen Central Venous Catheterization Kit* (circa 1986).

Arrow International, Inc., *The Arrow Multi–Lumen Catheter System* (circa 1986).

Arrow International, Inc., 510(k) Notification Multi–Lumen M.I.S.™ Catheterization System (Apr. 14, 1982).

Arrow International, Inc., 510(k) Notification Arrow Central Venous Multi–Lumen Catheter with Flex Tip (Aug. 25, 1986).

Arrow International, Inc. Arrow®–Howes™ Multi–Lumen Central Venous Catheterization Kit (circa 1986).

Arrow International, Inc., The Arrow Multi–Lumen Catheter System (circa 1986).

Arrow International, Inc., Anesthesia and Critical Care Catheterization Products, Hospital Price Schedule (May 1988).

American Edwards Laboratories, EDSLAB Thermodilution and Monitoring Catheters (circa 1982).

American Edwards Laboratories, The EDSLAB 6F Thermodilution Catheter (May 1980).

American Edwards Laboratories, EDSLAB Thermodilution and Monitoring Catheters (circa 1982).

American Edwards Laboratories, The EDSLAB 6F Thermodilution Catheter (May 1980).

American Edwards Laboratories, The EDSLAB 7F Thermodilution Catheter (Jul. 1980).

American Edwards Laboratories, Thermodilution Catheter Drawings (Sep. 2, 1976).

Eric A. Bour et al., Experience With The Double Lumen Silastic® Catheter for Hemoaccess, Surgery, Gynecology & Obstetrics 33 (Jul. 1990).

Todd L. Demmy & David V. Feliciano, A Modified Technique for Changing Triple–Lumen Catheters, Surgical Rounds 58 (Nov. 1988).

Stephen P. Gatt, A Quadruple–Lumen Intravenous Infusion Catheter, 11 Anaesth Intens Care 261–62 (1983).

Alan C. Geiss & Patrick P. Montefusco, Placement of an Implantable Percutaneous Permanent Triple–Lumen Catheter, 149 The American Journal of Surgery 395 (Mar. 1985).

Harold W. Horowitz et al., Central Catheter–Related Infections: Comparisons of Pulmonary Artery Catheters and Triple Lumen Catheters for the Delivery of Hyperalimentation in a Critical Care Setting, 14 J. of Parenteral and Enteral Nutrition 588 (Nov./Dec. 1990).

Jeffrey L. Kaufman et al., Clinical Experience with the Multiple Lumen Central Venous Catheter, 10 J. of Parenteral and Enteral Nutrition 487 (Sep./Oct. 1986).

Jean–Jacques Lanore et al., Hemodialysis for Acute Renal Failure in Patients with Hematologic Malignancies, 19 Critical Care Medicine 346 (Mar. 1991).

Sakharam D. Mahurkar & G. Dunea, Abstract of Parallel Lumen Continuous Flow Single Needle for Hemodialysis, in 5 Abstracts, ASAIO 22nd annual Meeting, San Francisco, Cal. (Apr. 1–3, 1976).

Sakharam D. Mahurkar, The Fluid Mechanics of Hemodialysis Catheters, XXXI Trans. Am. Soc. Artif. Intern. Organs 757 (1985).

Mary C. McCarthy et al., Prospective Evaluation of Single and Triple Lumen Catheters in Total Parenteral Nutrition, 11 J. of Parenteral and Enternal Nutrition 259 (Jun. 1987).

Henry D. McIntosh et al., Double Lumen Catheter for Use With Artificial Kidney, 169 J.A.M.A. 137 (Feb. 21, 1959).

Mitchell N. Ross et al., Comparison of Totally Implanted Reservoirs with External Catheters as Venous Access Devices in Pediatric Oncologic Patients, Surgery, Gynecology & Obstetrics 141 (Aug. 1988).

W. B. Saunders, *Dorland's Illustrated Medical Dictionary* 274 (25th ed. 1974).

Seigi Tsuchida et al., Single Two–Lumen Cannula Dialysis, 114 J. Exp. Med. 189 (1974).

Barry M. Brenner & Floyd C. Rector, Jr., *The Kidney* vol. II, p. 1684 (1976).

Arrow International, Inc., Anesthesia and Critical Care Catheterization Products, Hospital Price Schedule (May 1988).

* cited by examiner

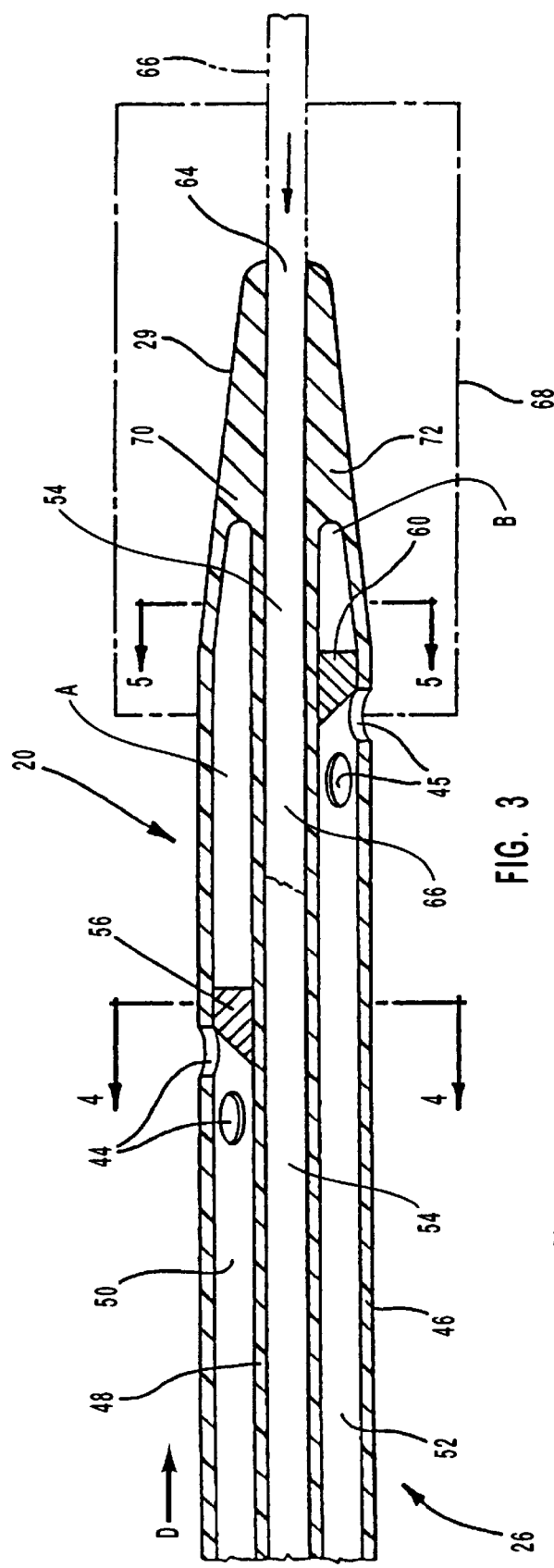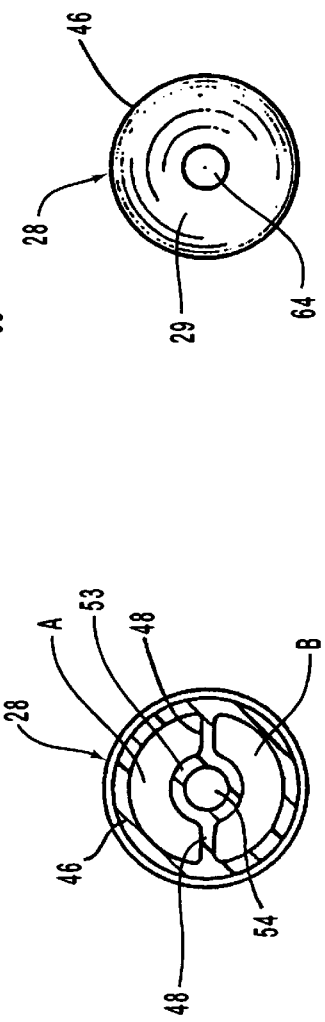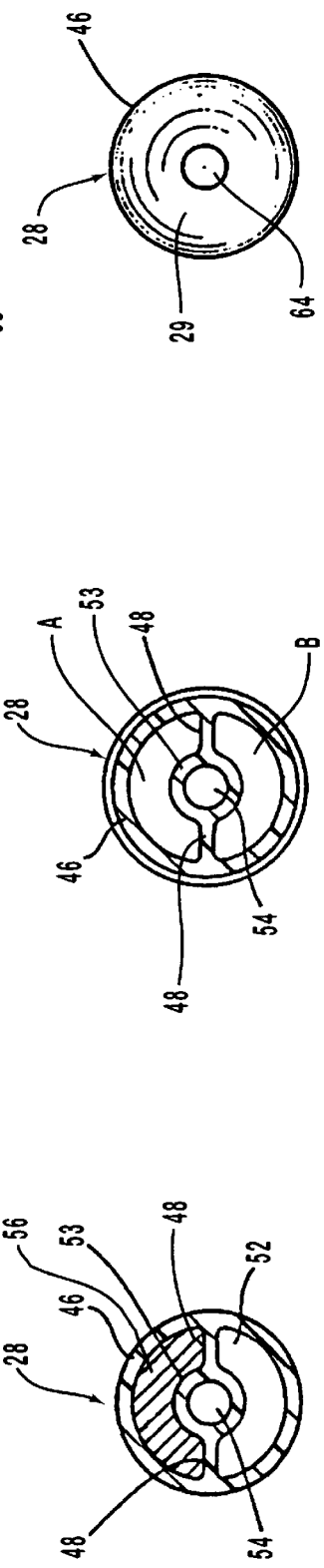

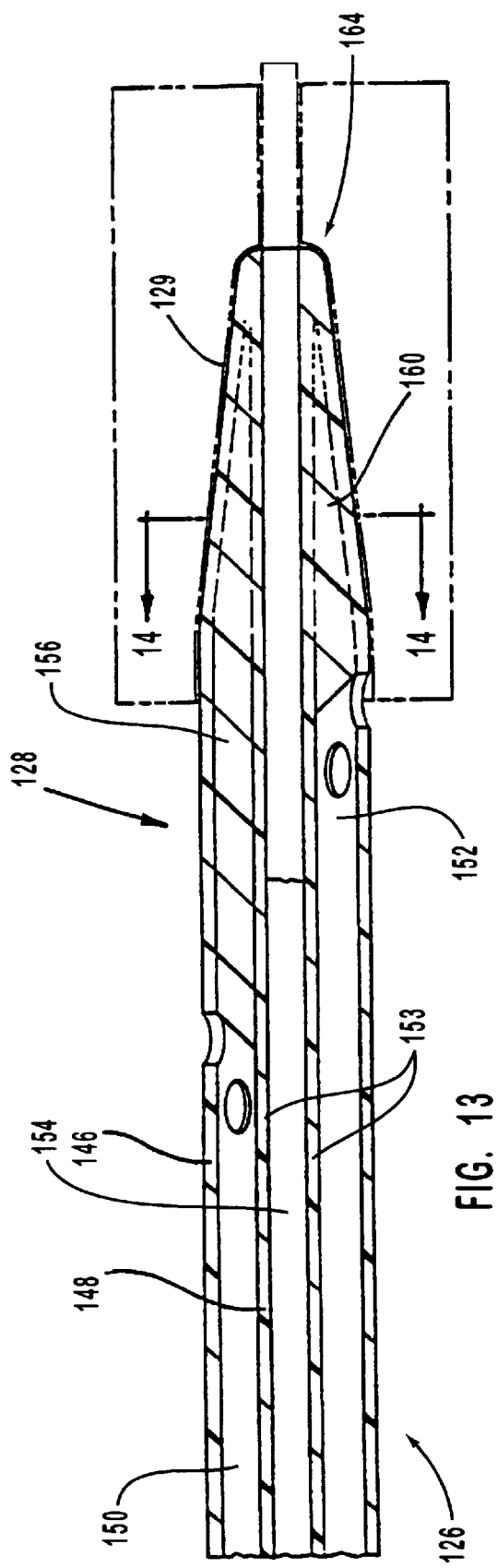
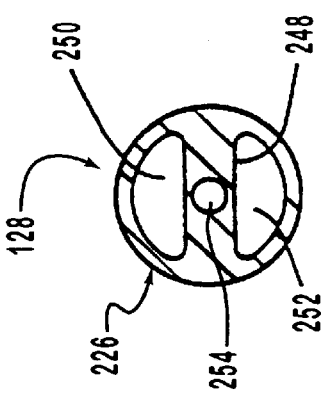
FIG. 13
FIG. 14
FIG. 15

MULTIPLE LUMEN CATHETER

RELATED APPLICATIONS

This application is a continuation application of U.S. patent application Ser. No. 08/481,169 that was filed on Jun. 7, 1995 (hereinafter "the Parent Application"), and that issued as U.S. Pat. No. 5,797,869 on Aug. 25, 1998. The Parent Application is a continuation application of U.S. patent application Ser. No. 08/205,331 that was filed on Mar. 3, 1994 (hereinafter "the Grandparent Application"), and that issued as U.S. Pat. No. 5,472,417 on Dec. 5, 1995. The Grandparent Application is a continuation application of U.S. patent application Ser. No. 07/785,351 that was filed on Oct. 30, 1991, (hereinafter "the Great-Grandparent Application") and that is now abandoned. The Great-Grandparent Application is a continuation application of U.S. patent application Ser. No. 07/288,364 that was filed on Dec. 27, 1988 (hereinafter "the "Great-Great-Grandparent Application"), and that issued as U.S. Pat. No. 5,195,962 on Mar. 23, 1993. This application is also related to U.S. patent application Ser. No. 07/699,421 that was filed on May 31, 1991, as a divisional application of the Great-Great-Grandparent Application and that issued as U.S. Pat. No. 5,135,599 on Aug. 4, 1992.

BACKGROUND OF THE INVENTION

This invention relates to a multiple lumen catheter and more particularly to such a catheter for insertion into a vein of a patient to be used in haemodialysis treatments. The invention also relates to methods for manufacturing the multiple lumen catheter.

FIELD OF THE INVENTION

Multiple lumen catheters have been available for many years for a variety of medical purposes. It is only in recent years, however, that such catheters have been developed for use in haemodialysis. The general form of multiple lumen catheters goes back to as early as 1882 when Pfarre patented such a catheter in the United States under U.S. Pat. No. 256,590. This patent teaches a flexible dual lumen catheter which is used primarily for cleaning and drainage of, for example, the bladder, rectum, stomach and ear. In this type of catheterization, the catheter is introduced into an existing body orifice without the use of any puncturing needle or guidewire.

More recently, a catheter was developed and patented by Blake et al under U.S. Pat. No. 3,634,924. This 1972 patent teaches a double lumen cardiac balloon catheter which is introduced into a large vein and the balloons inflated to control the flow in the vein. The catheter can in fact be placed by using the balloon as sails to move with the blood into or through the heart to a position where the catheter takes up its intended function. This patent uses two lumens and teaches a method of making a tip which involves the use of a plug and a wire which retains the shape of one of the lumens during formation of the tip in a moulding technique.

Further patents which teach multiple lumen catheters for general use include the following U.S. Pat. Nos.: 701,075; 2,175,726; 2,819,718; 4,072,146; 4,098,275; 4,134,402; 4,406,656 and 4,180,068.

Vascular catheter access by surgical cut-down techniques has been known to the medical profession for many years and, in fact, can be traced back to the 17th century. However, it was only with the introduction of the Seldinger technique in 1953 or thereabouts that a new approach could be used to improve vascular access. This technique was taught in an article published by Seldinger resulting from a presentation made at the Congress of the Northern Association of Medical Radiology at Helsinki in June of 1952. The technique essentially involves the use of a hollow needle to make an initial puncture and then a wire is entered through the needle and positioned in the vessel. The needle is withdrawn and the catheter is entered percutaneously over the wire which is later withdrawn. With this technique it became possible to make less traumatic vascular access and has now become the accepted method of performing access in numerous medical techniques. One of these techniques which has been the subject of much research and development, is haemodialysis.

Haemodialysis can be defined as the temporary removal of blood from a patient for the purpose of extracting or separating toxins therefrom and the return of the cleansed blood to the same patient. Haemodialysis is indicated in patients where renal impairment or failure exists, that is, in cases where the blood is not being properly or sufficiently cleansed, (particularly to remove water) by the kidneys.

In the case of chronic renal impairment or failure, haemodialysis has to be carried out on a repetitive basis. For example, in end stage kidney disease where transplantation of kidneys is not possible or for medical reasons is contraindicated, the patient will have to be dialysed about 100 to 150 times per year. This can result in several thousand accesses to the blood stream to enable the active haemodialysis to be performed over the remaining life of the patient.

Towards the end of 1960, Dr. Stanley Shaldon and colleagues developed, in the Royal Free Hospital in London, England, a technique for haemodialysis by percutaneous catheterization of deep blood vessels, specifically the femoral artery and vein. The technique was described in an article published by Dr. Shaldon and his associates in the Oct. 14th, 1961 edition of The Lancet at pages 857 to 859. Dr. Shaldon and his associates developed single lumen catheters having tapered tips for entry over a Seldinger wire to be used in haemodialysis. Subsequently, Dr. Shaldon and his colleagues began to insert both inlet and outlet catheters in the femoral vein and this was reported in the British Medical Journal of Jun. 19th, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to haemodialysis equipment periodically.

Some use was made of a flexible dual lumen catheter inserted by surgical cut-down as early as 1959. An example of such a catheter is that of McIntosh and colleagues which is described in the Journal of the American Medical Association of Feb. 21, 1959 at pages 137 to 138. In this publication, a dual lumen catheter is made of non-toxic vinyl plastic and described as being inserted by cut-down technique into the saphenous vein to the inferior vena cava.

The advantages of dual lumen catheters in haemodialysis is that only one vein access need be affected to establish continued dialysis of the blood, because one lumen serves as the conduit for blood flowing from the patient to the dialysis unit and the other lumen serves as a conduit for blood returning from the dialysis unit to the patient. This contrasts with prior systems where either two insertions were necessary to place the two catheters as was done by Dr. Shaldon, or a single catheter was used with a complicated dialysis machine which alternatively removed blood and returned cleansed blood.

The success of Dr. Shaldon in placing catheters which will remain in place for periodic haemodialysis caused further work to be done with different sites. Dr. Shaldon used the femoral vein and in about 1977 Dr. Uldall began clinical testing of a subclavian catheter that would remain in place. An article describing this was published by Dr. Uldall and others in Dialysis and Transplantation, Volume 8, No. 10, in October 1979. Subsequently Dr. Uldall began experimenting with a coaxial dual lumen catheter for subclavian insertion and this resulted in Canadian Patent No. 1,092,927 which issued on Jan. 6, 1981. Although this particular form of catheter has not achieved significant success in the marketplace, it was the forerunner of dual lumen catheters implanted in the subclavian vein for periodic haemodialysis.

The next significant step in the development of a dual lumen catheter for haemodialysis is U.S. Pat. No. 1,150,122 to Martin who produced a catheter which achieved some commercial success. The catheter avoided the disadvantages of the Uldall structure.

A subsequent development is shown in U.S. Pat. No. 4,451,252 also to Martin. This utilizes the well known dual lumen configuration in which the lumens are arranged side-by-side separated by a diametric septum. The structure shown in this patent provides for a tip making it possible to enter a Seldinger wire through one of the lumens and to use this wire as a guide for inserting the catheter percutaneously. Patents to this type of structure followed and include European Patent Application to Edelman published under No. 0 079 719, U.S. Pat. Nos. 4,619,643; 4,583,968; 4,568,329 and U.S. Design Pat. No. 272,651.

All of the above examples of haemodialysis catheters suffer from the disadvantages that they can not be used readily for intravenous injection of liquid medication. A person who is using haemodialysis therapy with a dual lumen catheter will have to receive a needle for intravenous injection when medication of this kind is required. It would be desirable that the catheter not only perform the function of haemodialysis, but also provide a facility for intravenous injection without further puncturing of the patient's veins. It is one of the objects of the present invention to provide such a catheter.

The foregoing problems associated with haemodialysis catheters may on some instances be specific to the treatment. However, the catheter of the present invention, in overcoming the disadvantages of the prior art of renal dialysis catheters, provides a catheter which has utility in other procedures. Accordingly, although the present description is directed to haemodialysis, such use is exemplary and it will be evident that catheters according to the invention may be used for other procedures.

BRIEF DESCRIPTION OF THE DRAWINGS

These and other aspects of the invention will now be described with reference to the accompanying drawings, in which:

FIG. 3 is an enlarged sectional view of the distal end of the catheter of FIG. 1 drawn on line 3—3 of FIG. 2;

FIGS. 4 and 5 are enlarged sectional views taken on the lines 4—4, 5—5 of FIG. 3, respectively, and showing complete sections;

FIG. 6 is an end view of the catheter in the direction generally of arrow of FIG. 3;

FIG. 13 is a view similar to FIG. 3 of the distal end of another embodiment of the present invention;

FIG. 14 is a sectional view taken on line 14—14 of FIG. 13;

FIG. 15 is a sectional view of a further embodiment of the catheter;

DESCRIPTION OF PREFERRED EMBODIMENTS

The invention will be described in detail with reference to a preferred embodiment to be used for haemodialysis. However the drawings and description are exemplary of the invention and unless otherwise stated, are not intended to be limited by its restraints of size and properties dictated by haemodialysis procedures.

Figure 1:
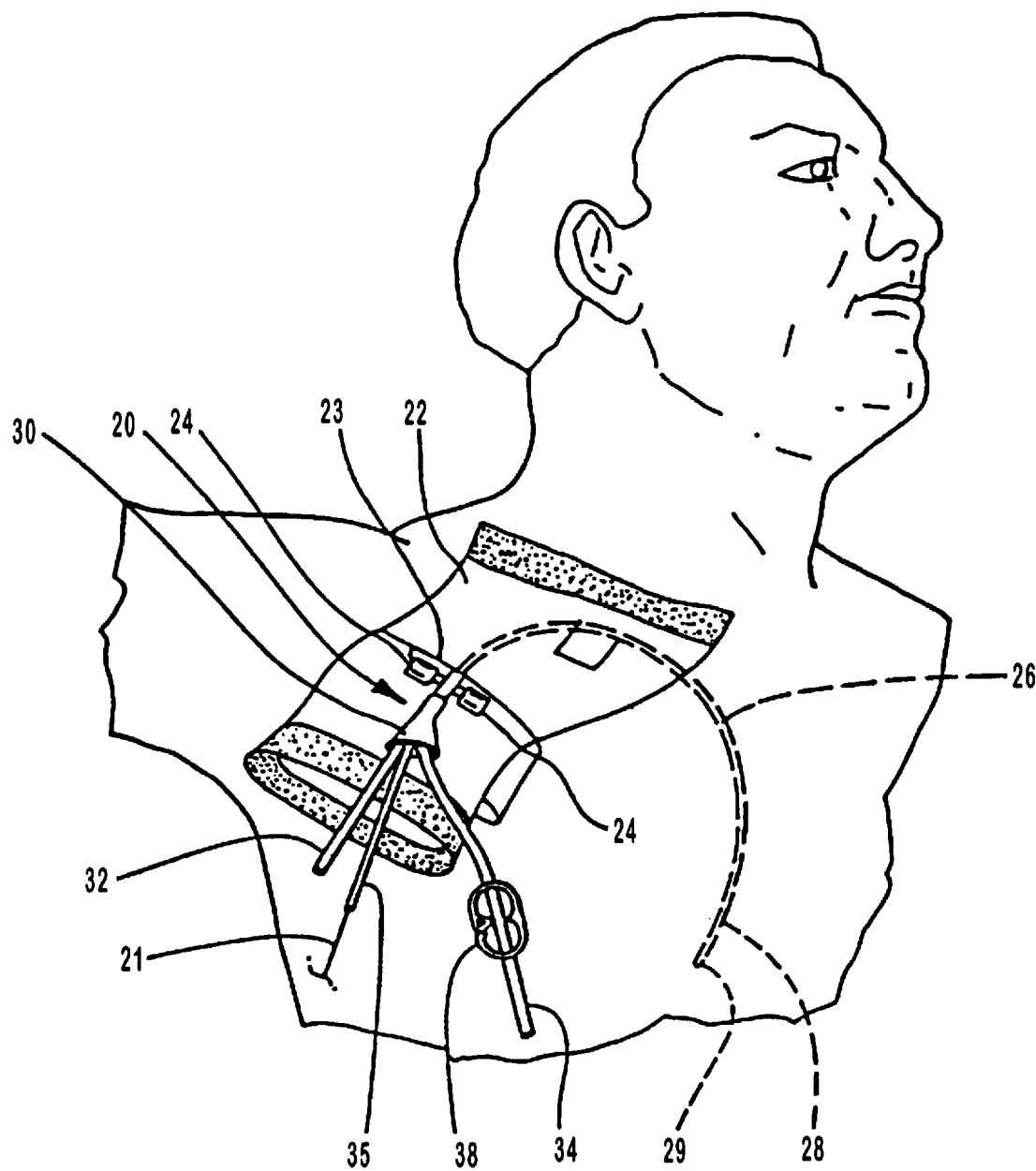
FIG. 1 is a diagrammatic view of a triple lumen catheter according to a preferred embodiment of the present invention, inserted into the subclavian vein of a patient.

Reference is made first to FIG. 1 of the drawings which illustrates a triple lumen catheter, indicated generally by reference numeral 20, according to a preferred embodiment of the present invention, and showing by way of example, a patient receiving the catheter in the subclavian vein using a Seldinger wire 21. The catheter is to be used for haemodialysis treatment and could of course also be entered in a similar fashion in the femoral vein.

The catheter 20 is secured to a conventional dressing 22 by an attachment fitting 23 having wing tabs 24, and the dressing 22, in turn, is secured to the skin of the patient. As shown, the catheter 20 passes through the dressing 22 and, as can be seen in broken outline, an elongate and flexible cylindrical body 26, formed of a polyurethane extrusion, is inserted through the skin and into the subclavian vein in the downstream direction. The catheter 20 has at its distal end 28 a conical tapered tip 29 which is described in greater detail below. The other end of the body 26 is a generally trident-shaped branching connector 30, which protrudes outwardly from and is secured by dressing 22. Cylindrical blood extraction and return tubes 32, 34 and an intravenous (IV) tube 35 are attached to the trident-shaped branching connector 30, a full description of which is provided below. For the moment it is sufficient to state that these tubes are connected to lumens running through the body 26.

Figure 2:
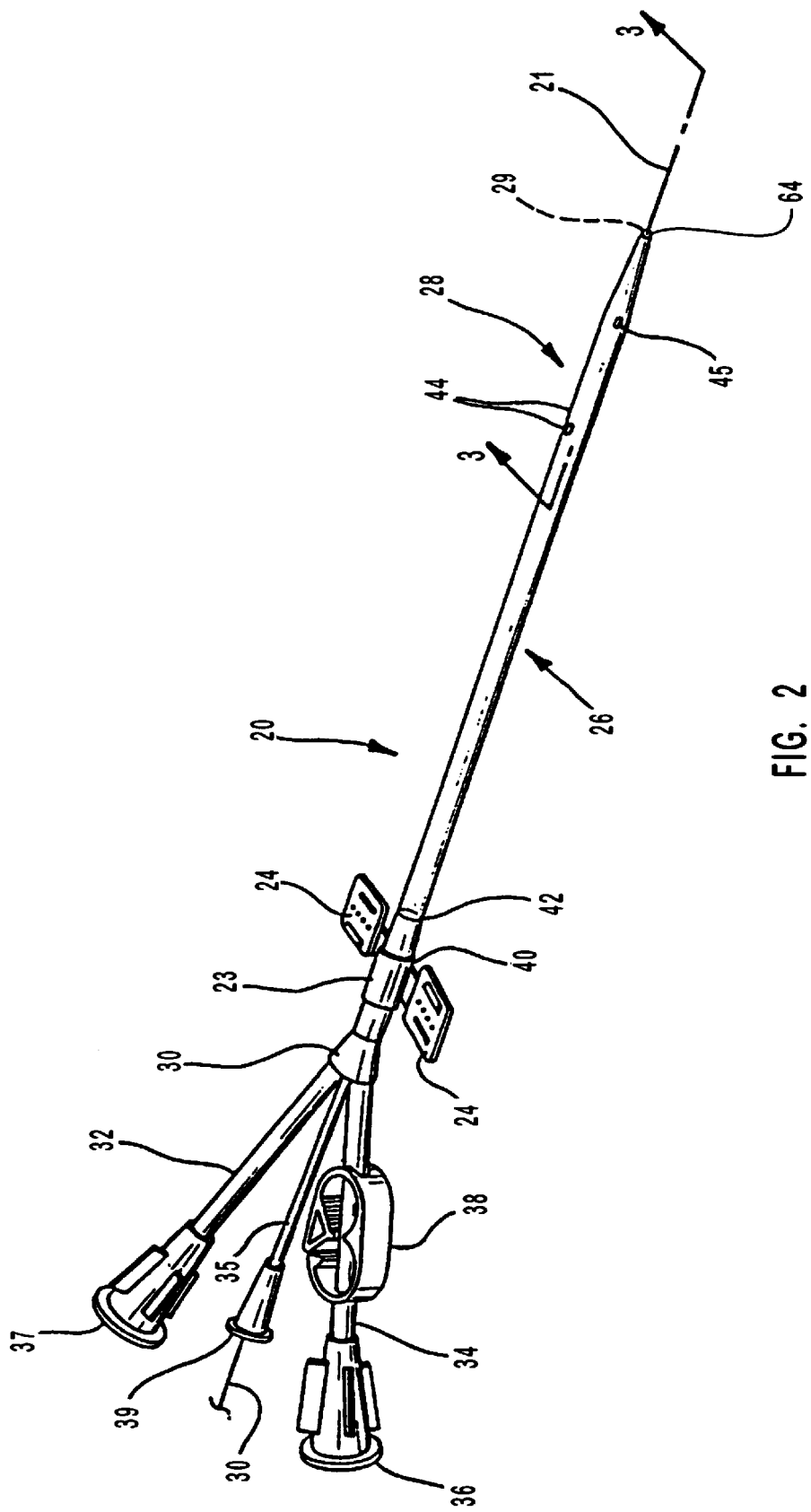
FIG. 2 is a diagrammatic perspective view of the catheter drawn to a larger scale than that used in FIG. 1.

FIG. 2 shows the catheter 20 in greater detail. The body 26 has at its proximal end the connector 30 for receiving the blood extraction and return tubes 32, 34. These tubes terminate at their outer ends in respective female luer fittings 36, 37 for connection to complementary male luer fittings (not shown) leading to a dialysis machine, and carry closure clamps 38 (one of which is shown) to selectively close the tubes.

The IV tube 35 terminated at its outer end in a luer lock fitting 39 for receiving a syringe or male luer lock connector.

The wing tabs 24, sometimes known as suture wings, are formed integrally with a central tubular portion 40 which can rotate on the body 26 and is retained in place by a shoulder on the end of the connector 30 and a second shoulder in a reinforcing portion 42 so that the catheter 20 can be rotated relative to the tabs 24. This rotation is sometimes necessary after insertion of the catheter 20 to re-orientate intake side apertures in the distal end 28 if the apertures happen to be occluded by engagement with the wall of the vein. Details of the apertures are provided below.

As will be described, the reinforcing portion 42 is blended into the body 26 over the length of the portion and assists in strengthening the catheter to minimize the likelihood of kinking. Also, the portion 42 assists in sealing the puncture site where the catheter enters the patient.

As will be described in more detail with reference to subsequent views, the tube 35 is aligned with a central lumen to permit the Seldinger wire 21 to pass through the catheter. The wires exists distal end 28 of catheter body 26 through a tip aperture 64 at the apex of tip 29 which is essentially conical so that the catheter can slide over the wire and into the patient during insertion. The extraction and return tubes 32, 34 are linked at connector 30 with lumens in the body 26 to connect with respective groups of side apertures 44, 45 (some of which can be seen in this view) near the distal end of the catheter 28. As a result, when inserted and in use, blood can be removed and returned in a closed loop with a haemodialysis machine using the tubes 32, 34. Between treatments the tube 35 is available for intravenous infusion of liquid medicaments.

Reference is next made to FIGS. 3 to 6 of the drawings which illustrate the distal end 28 including tip 29. The body 26 comprises an outer wall 46 and an integral septum 48 extending diametrically across the body 26 and defining an extraction lumen 50 and a return lumen 52, both lumens being generally C-shaped in cross-section and extending from the proximal end towards the distal end. As best seen in FIG. 4, a bulbous middle portion 53 of the septum 48 projects into the lumens 50, 52 and contains the intravenous (IV) lumen 54 which extends along the longitudinal axis of the body portion 26 from the proximal end to the distal end. This lumen is an extension of the IV tube 35 and is proportioned in this embodiment to receive a 0.038 inch diameter Seldinger wire.

The extraction lumen 50 is blocked short of the tip 29 by a first insert 56 which is formed of polyurethane and bonded in place using a suitable solvent such as cyclohexanane, leaving a hollow extension A of extraction lumen 50 distal of first insert 56. Extraction apertures 44 are provided in the outer wall 46 of the cylindrical portion 26, just short of the insert 56, to permit blood to flow from the patient's vein into the extraction lumen 50 and thus through the connector 30 to the extraction tube 32 and the dialysis machine. It should be noted that the apertures 44 are conveniently circular but may be of any suitable shape or size including scaphoid. Also, further extraction apertures may be provided around the lumen 50 as required consistent with the aperture nearest the tip being immediately adjacent the insert 56 to minimize dead spaces.

The return lumen 52 is similarly blocked by a second insert 60 immediately adjacent the last of several return apertures 45. This last aperture is positioned closer to the tip 29 than is the last of the intake apertures 44 in the extraction lumen 50 to minimize the risk of cross flow as returning blood finds its way back into the lumen 50. A hollow extension B of return lumen 52 remains distal of second insert 60. Although some cross-flow is not critical, excess cross-flow will extend the time needed for haemodialysis.

As can be seen in FIGS. 3 and 6, the tip 29 is smoothly rounded at the end 28 of the catheter and tapered slightly gently to facilitate insertion of the catheter 20 into a patient. As mentioned previously, the catheter is intended to be used with a Seldinger wire. It is, therefore, clearly desirable that the tapered tip 29 be concentric with the axis of the body 26 and of the lumen 54. Accordingly, the centrally located IV lumen 54 extends to the tip 29 and terminates at a circular IV aperture 64.

The catheter 20 is made from a length of cylindrical polyurethane extrusion forming the cylindrical body 26. The extrusion is cut to the required length and the ends formed by further operations. The formation of the tapered tip 29 will be described with reference firstly to FIG. 3, followed by a description of the formation of the connector 30.

Before shaping the tapered tip 29, the inserts 56, 60 are positioned and affixed in the respective lumens 50, 52 as shown in FIG. 3. The inserts are shaped to the cross-section of the lumens and affixed as previously described. A cylindrical wire 66 (shown in chain dotted outline), of corresponding diameter to that of the guide wire 21 (FIG. 2), is inserted through the IV lumen 54 to extend from the distal end of the tubing which is then located in a conical tapered mould 68 (shown in chain-dotted outline). The extrusion is heated by R.F. and as it softens it is pushed into the mould 68 in the direction of arrow D, such that the outer wall 46 and the septum 48 merge at the tip 29. The end of the body assumes a conical tapered shape with a radiused end and the material masses in the lumens 50, 52 forming ends 70, 72. The IV lumen 54 retains its internal shape because it is supported on the wire 66. The now tapered tip is cooled to some extent and then removed from the mould 68 and allowed to cool further and harden.

The deformation of the tip results in a thickening of the outer wall 46 and septum 48 to provide a concentration of material substantially exceeding the concentration of material in the main catheter body, and this has the effect of stiffening the tip, which facilitates insertion of the catheter.

Because the wire 66 is not deflected at any time from its normal straight condition during the moulding operation, there is no energy stored in the wire and consequently there is no tendency for the wire to deflect the tip from the desired orientation after removal from the mould 68.

The wire can therefore be left inside the tip during cooling. The apertures 44, 45 are then cut or otherwise formed in the outer wall 46 of the body 26. Also, because the extrusion is symmetrical about the wire, the deformed material at the tip will move evenly to each side of the central septum. The resulting similar masses at ends 70, 72 of the lumens will cool and shrink equally so that the tip will remain concentric about the central or IV lumen 54. This will result in a well formed tapered tip.

The method of manufacture of the trident-shaped branching connector 30 and reinforcing portion 42 will next be described with reference to FIGS. 7 to 12. The figures are arranged in order of the steps used in the manufacture and it will be seen in FIG. 7 that the extruded body 26 has received a short sleeve 71 of polyurethane and preferably the same color as that used for the body. The sleeve 71 is a snug fit on the cylindrical body 26 and after positioning on the body, the assembly is moved into a heated moulded 73 which has a frustro-conical interior wall 75 designed to deform the sleeve 71 to create the blended reinforcing portion 42 shown in FIG. 2. If preferred, suitable shaped mandrels can be placed inside the lumens of the body 26 to ensure that the lumens are not deformed while the collar is shaped in the mould 73. The sleeve 71 is heated and the body pushed into the heated mould 73 so that material flows to the desired shape.

The upper edge of the sleeve 71 (as drawn) forms a shoulder and is positioned for engagement with the attachment fitting 23 shown in FIG. 2 to locate this fitting longitudinally on the body.

Figure 7:
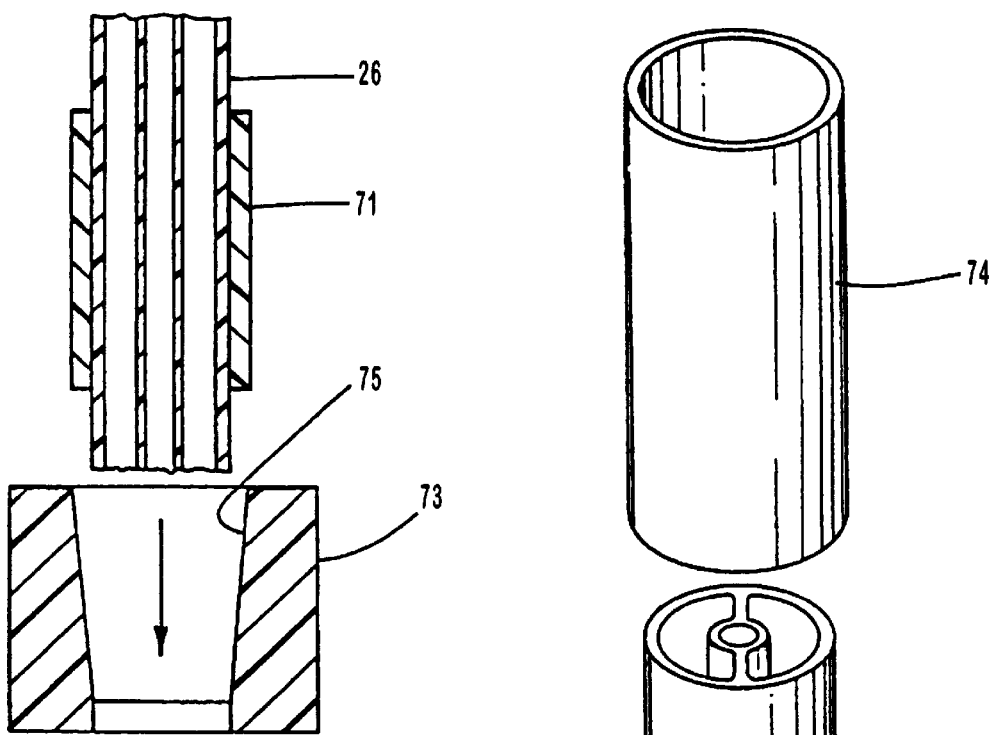
FIG. 7 is a sectional view of a trident-shaped branching connector seen at the proximal end of the catheter in FIG. 2 and drawn to a larger scale.
Figure 8:
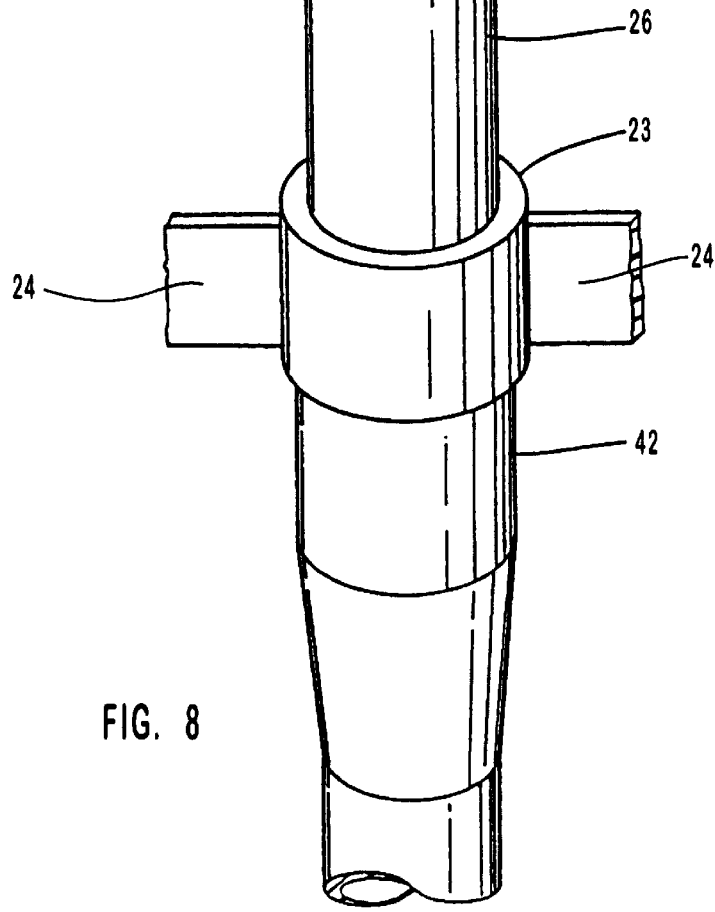
FIGS. 8, 9, 10 and 11 are diagrammatic perspective views of an end of the catheter showing the various steps in the manufacture of the trident-shaped branching connector and associated parts.

After completing the process illustrated in FIG. 7, the fitting 23 is slipped over the end of the body 26 and into engagement with the sleeve 71. The fitting is a loose fit so that it can rotate freely on the body 26. The positioning can be seen in FIG. 8 which also shows the completed reinforcing portion 42 and how it blends into the body 26.

Figure 9:
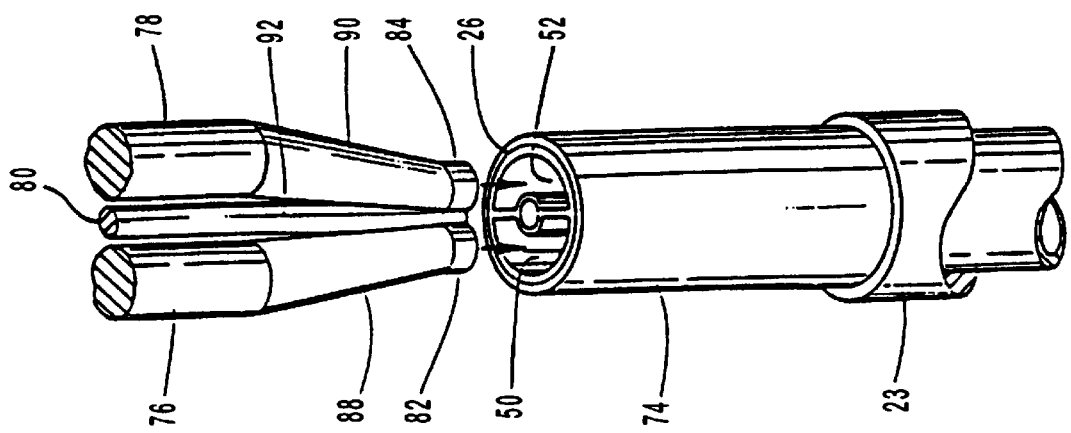

Next another sleeve 74 is engaged over the end of the tube 26 and, if the first sleeve has been positioned correctly, the sleeve 74 will be positioned so that its trailing end becomes flush with the end of the body 26 as shown in FIG. 9. The sleeve 74 should not be pushed tightly against the attachment fitting 23 in order to provide clearance of free movement of the fitting. With the sleeve in position, a set of deforming mandrels are brought into play as seen in FIG. 9. There are three mandrels, one for each of the lumens. The two outer mandrels 76, 78 are mirror images of one another and positioned about a central mandrel 80. The intent of the mandrels is to form the corresponding lumens to have conical outer portions for receiving shaped ends of the tubes 32, 34 and 35 (FIG. 2) as will be described with reference to FIG. 12.

The mandrels 76, 78 have respective leading ends 82, 84 which are proportioned simply to provide location as they enter corresponding lumens 50, 52 and similarly, a leading portion 86 on the mandrel 80 is proportioned to engage the central lumen 54. The leading portions 82, 84 and 86 blend into respective conical portions 88, 90 and 92 which are arranged to complement one another so that the cones will flair outwardly to receive the tubes. Of course for simplicity of engagement, each of the mandrels is supported from shanks which are arranged in parallel so that the mandrels can be brought into the extrusion longitudinally and deformation will take place simply because the conical portions are larger than the lumens and the material around the lumens will be forced outwardly under the influence of heat provided by heating the mandrels. The second sleeve 74 supports the extrusion which is itself insufficient to support this deformation as the size is increased.

Figure 11:
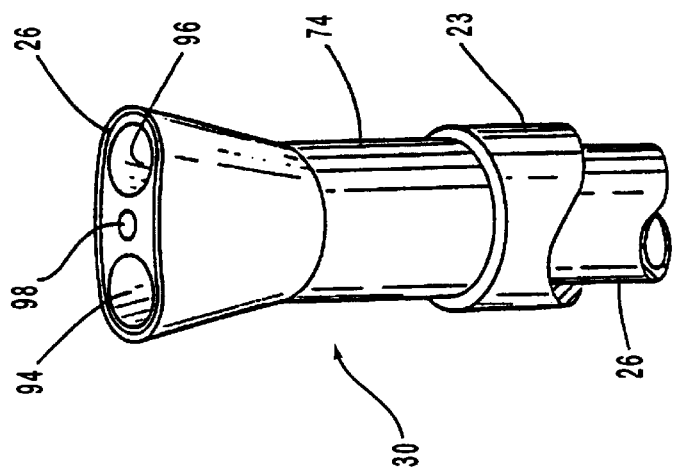
Figure 10:
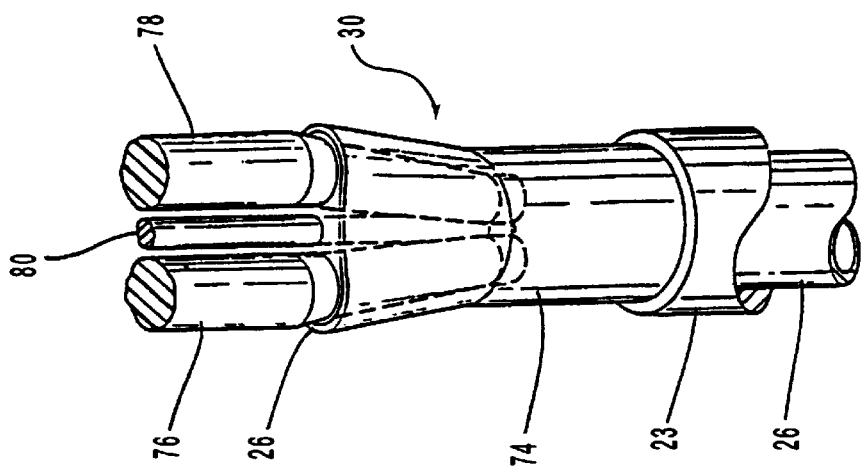

It will be seen in FIG. 10, that after the mandrels are engaged, the second sleeve 74 and contained portion of the extrusion are expanded to form connector 30 and, after completion, the appearance of connector 30 will be as shown in FIG. 11.

Figure 12:
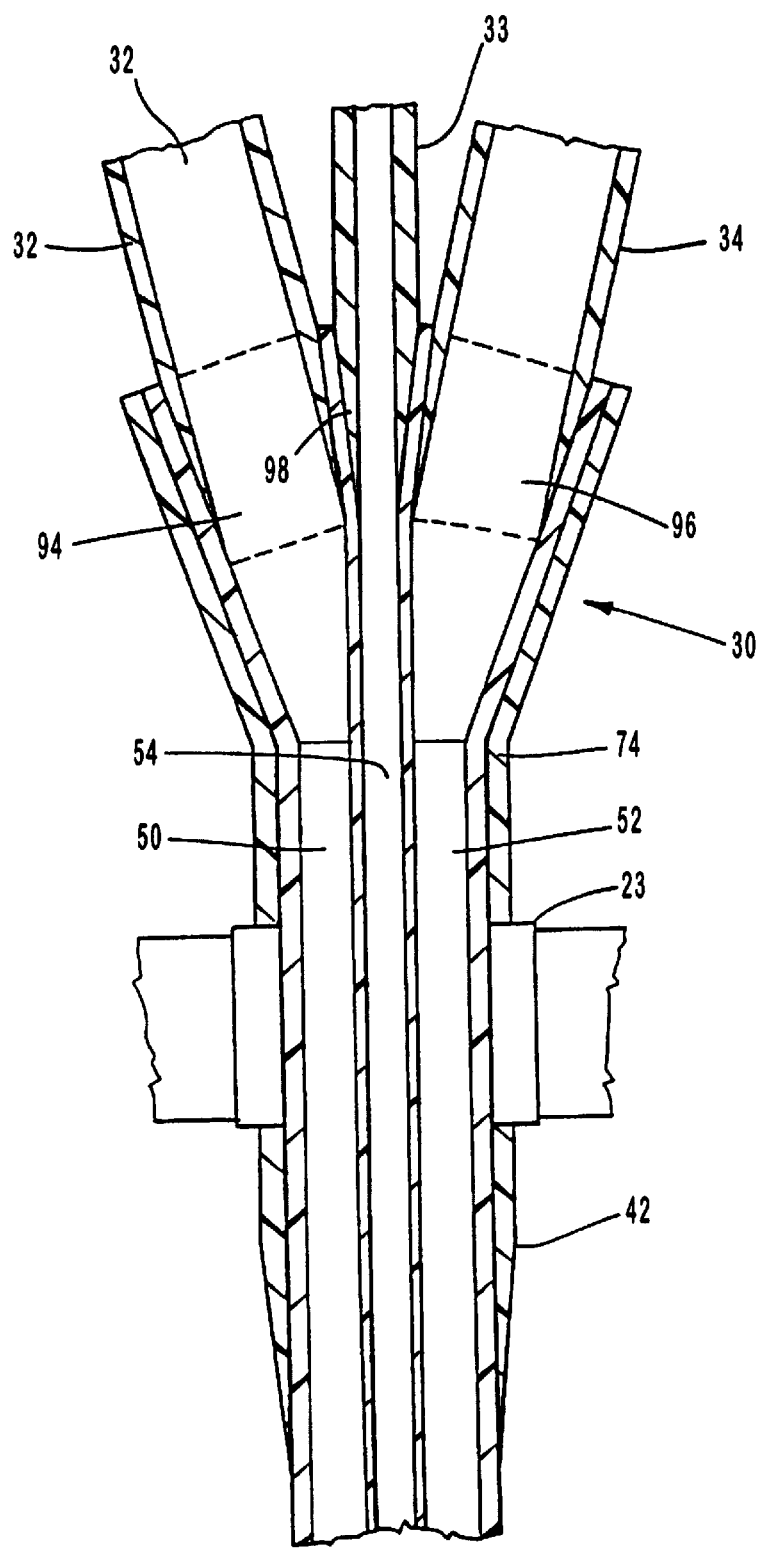
FIG. 12 is a sectional view of the connector after assembly.

Reference is next made to FIG. 12 which shows the engagement of the tubes 32, 34 and 35 in the connector 30. These tubes have their engagement ends deformed to thin the wall and this is done by conical deformations so that the outer surface of the tubes are slightly conical to engage the corresponding internal cones 94, 96 and 98 shown in FIG. 11 and formed by the use of the mandrels. It will be seen in FIG. 12 that the result in assembly is compact, and provides a relatively smooth internal surface to minimize the risk of blood damage caused by turbulence as blood flows through the tubes and associated lumens 32, 34 and 50, 52. Similarly, the tube 35 is engaged so that there is no interference with the Seldinger wire which will slide freely through this tube and lumen 54.

The tubes are attached in the connector 30 using a suitable solvent in a similar fashion to the attachment of the plugs 56, 60 described with reference to FIG. 3.

It is of course possible to make the assembly starting with the trident shaped structure and then add the fitting 23 from the distal end of the body before ending by adding and forming sleeve 71.

In use, as mentioned above, the catheter 20 is inserted such that it points downstream in the patient's vein, that is, the extraction aperture 44 are upstream of the return apertures 45, which, in turn, are upstream of the IV tip aperture 64. When a treatment is in progress the extraction tubes 32, 34 are connected to a dialysis machine which draws blood through the extraction lumen 50 and returns it through return lumen 52 in a similar manner to a conventional dual lumen cannula. Between blood treatments the lumens may be filled with a heparin solution to prevent them from being filled with clotted blood. However, if the patient requires medication or is required to give blood between treatments, the IV lumen 54 may be used. This avoids the trauma and discomfort of inserting a further needle or catheter into the patient and does not disturb the heparin lock.

Between uses the third lumen may be filled with a relatively small volume of heparin or may be occupied by cylindrical solid and flexible patency obturator, similar to guide wire 21. This obturator prevents the entrance of blood into the lumen and thus eliminates the need for heparin in the third lumen. Generally, it will be easier to keep the third lumen free of blood due to its smaller cross-section, regular shape and absence of side holes.

In addition to this advantage the centrally located lumen offers considerable advantages for insertion and removal of the catheter. As there are no side holes in the lumen, "J" ended guide wires may be used without the possibility that the guidewire will exit through a side hole, rather than the end aperture. In addition, because it is easier to keep the smaller lumen free of clotted blood, it should be possible to use a guidewire to replace a catheter which has clotted blood in the blood lumens without dislodging any blood clots which may have accumulated in the blood lumens. This would be done by first entering the Seldinger wire into the third lumen of the catheter in place in the vein, withdrawing this catheter over the wire leaving the wire in place, and then using the wire to guide a replacement catheter over the guide wire.

The exemplary catheter described with reference to the drawings does not have the proportions of a haemodialysis catheter. As mentioned previously, the description is exemplary and in practice, if the catheter is to be used in the subclavian vein it will have proportions as follows. The central lumen will have a diameter of about 0.04 inches to receive a Seldinger wire of diameter 0.038 inches or 0.036 inches. The walls about the central lumen and forming the septum will be about 0.010 inches in thickness and will blend into the outer wall which is about 0.013 inches in thickness. The outer diameter of the body 26 will be 0.149 inches and this will give an area available for blood flow in the lumens of about 0.0048 square inches. The flow rate will be approximately 237 milliliters per minute using accepted pressures to drive the blood through the lumens.

Clearly catheters can be made with a variety of proportions depending upon the use and structures defined by the claims and incorporating the description are within the scope of the invention.

The tip structure shown in FIG. 3 can be made in a number of ways. An alternative is shown in FIGS. 13 and 14. For ease of reference the reference numerals used in relation to these figures correspond to those used above prefixed with the numeral 1. The distal end 128 and tip 129 of a catheter 126 has inserts 156, 160 which extend to fill the unused portions of the extraction and return lumens. The inserts are entered in the lumens 150, 152 and may be affixed therein by a solvent. When the end 128 is heated in the mould the inserts 156, 160 are softened and deformed and the outer wall 146 collapses to merge with the septum 148. The leading ends of the inserts 156, 160 also merge with the septum 148, as represented by the ghost outlines in FIGS. 13 and 14. The resulting catheter has an appearance similar to the catheter described above with a tip opening 164 but with a stiffer leading end.

It will be evident that the form of the inserts can vary. For instance the ends originally near the end 128 could be thinned to allow for easier deformation of the extrusion into the shape shown in FIG. 13.

The catheters illustrated and described above feature septums having a bulbous middle portion 153 to accommodate the IV lumen 154. However, the catheter of the invention is not limited to this particular cross-section and FIG. 15 shows an alternative cross-section. For ease of reference the numerals used in relation to this figure correspond to those used to describe the preferred embodiment prefixed with the numeral 2. The catheter 126 illustrated has a septum 248 with planar sides such that the extraction and return lumens 250, 252 have a D-shaped cross-section. This thicker septum 248 requires the use of more material to form the catheter and also reduces the ratio between the cross-sectional area of the extraction and return lumens and the cross-sectional area of the catheter. However, there may be uses above where this cross-section is advantageous, for instance, where the outer diameter of the catheter body is less critical than it is when used in a vein for haemodialysis.

Figure 16:
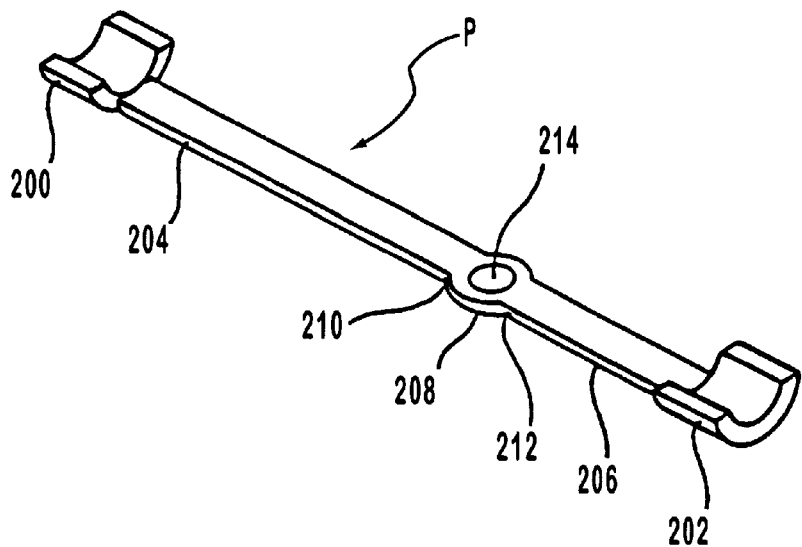
FIG. 16 is a perspective view of a plug for use in making yet another embodiment of the catheter.

Reference is now made to FIG. 16 to describe a moulded plug of polyurethane for use in making tips. This plug P has end pieces 200,202 shaped to fit snugly in the lumens 50, 52 (FIG. 3). The end pieces are attached to respective spacers 204,206 which depend from a hub 208 at respective weakened joints 210,212. The hub has a central opening 214 matching the third IV lumen 254 so that the wire used in moulding can be used to locate the hub centrally.

The procedure, when using the plug P of FIG. 16, is to first bend the spacers 204,206 about the joints 210,212 so that the end pieces 200,202 come together for insertion in the end of the extruded body 26. The pieces are pushed home with solvent until the hub 208 meets the end of the body. The pieces 200,202 will then automatically be in the required positions controlled by the lengths of the spacers 204,206. Moulding then proceeds as before so that the hub and adjacent parts of the spacers will become integral portions of the tip.

Figure 17:
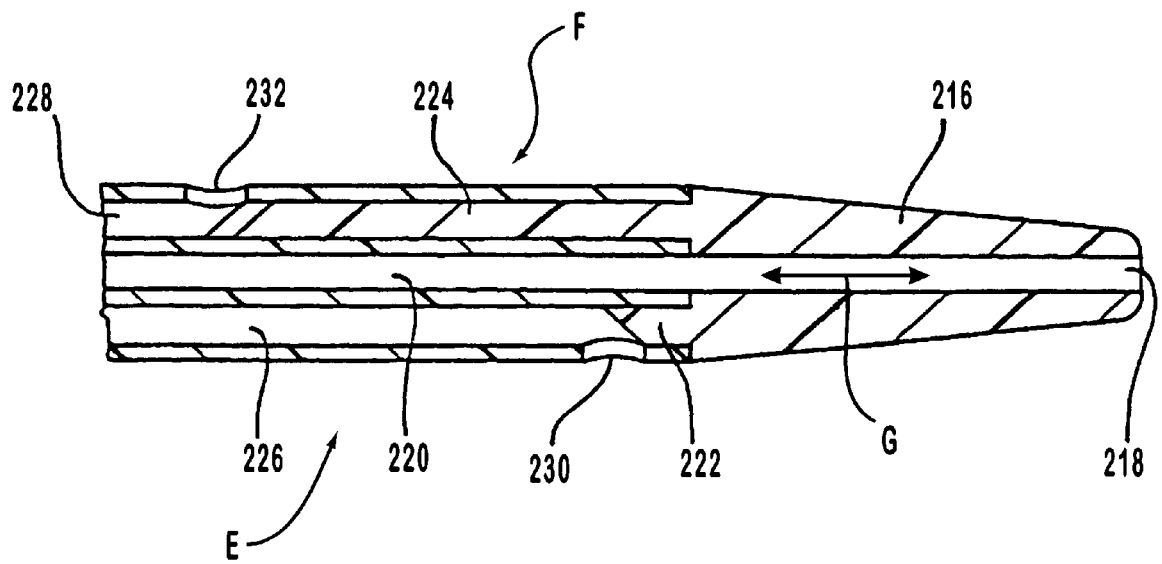
FIG. 17 is a sectional view of still another embodiment of the catheter and using a separate bonded tip.

A further embodiment is shown in FIG. 17. This structure includes a separate moulded tip 216 preferably of polyurethane, which is engaged in and bonded to the distal end F of an extruded catheter body E. The tip 216 has an outer conical form and defines a central opening 218 at one end of a central passageway G that forms a continuation of the third lumen 220. A pair of extensions 222, 224 are shaped to fit in the respective lumens 226, 228 and have lengths to match the positions of the apertures 230,232 in the side wall of the lumens. The ends of the extensions are preferably shaped to meet the apertures and complement the natural flow patterns so that dead spaces will be minimized, if not eliminated.

The structure shown in FIG. 17 can also be partly formed by heating in a mould to blend the joint between the tip and the extrusion. This technique can also be used to part form the assembly to improve the tip, if necessary.

The method of shaping the end is described as utilizing radio frequency heating devices to soften the plastic material. This is intended to be illustrative of a softening technique, and other techniques, for example, the use of electrical heating elements, are equally effective.

Figure 18:
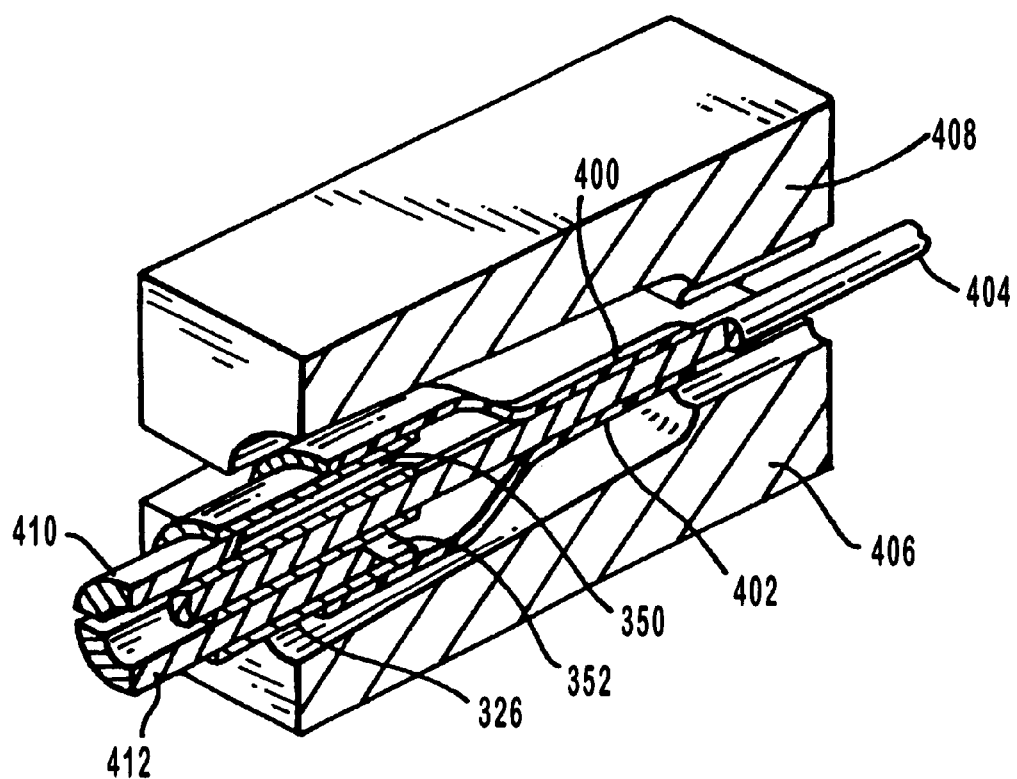
FIG. 18 is a sectional view illustrating an alternative method of manufacturing a tip according to the invention.

The third method of manufacturing the tip is illustrated in FIG. 18. Numerals corresponding to those used in FIG. 3 will be repeated with a prefix "3".

In this embodiment, a body 326 receives an extension piece 400 shaped to fit roughly on the end of the body and having a projection 402 of the shape needed as a continuation of the central aperture or third lumen. The parts are located relative to one another by a central rod 404 within two halves 406, 408 of a heated dye shaped to correspond to the tip shape shown in FIG. 3. This shape can of course be modified to provide varying ends on the catheter depending upon the desired configuration.

The body 326 receives first and second mandrels 410, 412 shaped to fit within the lumens 350, 352 and positioned so that material flowing under the influence of the heat will engage with the ends of the mandrels in a fashion corresponding to the plugs 56, 60 shown in FIG. 3. The result will be continuous material from the distal end of the catheter to the ends of the mandrels 410,412. The shaping can be seen in FIG. 3 but without the spacing between the plugs 56, 60 and the solid end of the catheter.

Under the influence of heat, the material of the body 326 and extension 400 will flow and be shaped by the closing dye halves 406, 408. The necessary quantity of material required to complete the shape can be augmented by the provision of plugs in the lumens 350, 352 of a material which will also flow under the influence of heat. However, with some care in design, it is possible to complete the tip without the use of these plugs.

The structure shown in FIG. 18 has the advantage that the extension 400 can be of any durometer hardness required, consistent of course with the material matching that of the body 326. Consequently, it is possible to create a distal end on the tip having different characteristics from the main body. The very end of the catheter can be quite soft so that, when it is inserted, it will have minimal strength and therefore reduce the risk of damage to the wall of the vein after insertion. Such a tip may well make it possible to leave the catheter in place for longer periods than would be possible with a tip having a stiff end.

Figure 19:
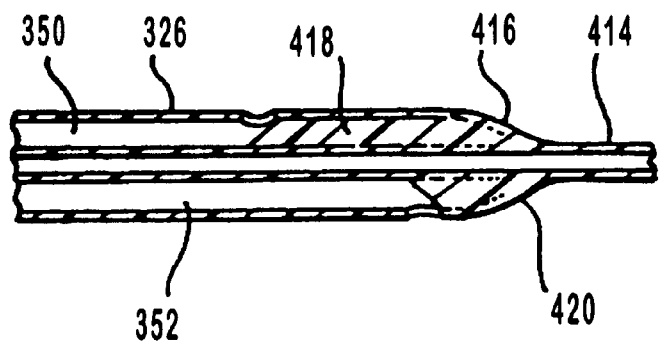
FIG. 19 is a side view of a tip made using the method illustrated in FIG. 18.

Reference is now made to FIG. 19 which illustrates a further embodiment of tip made using the method of FIG. 18. As mentioned, the mould house can be of different shapes and the shapes chosen to make the structure in FIG. 19 provide a cylindrical central extension 414 made from a part similar to that identified as 402 in FIG. 18. There is a transition zone defining a shoulder 416 where the extension 414 blends smoothly into the body 326. In this embodiment, to provide sufficient material to block the lumens 350, 352, plugs 418 and 420 are provided and these flow into the material around them as indicated by the broken outline at the shoulder 416. With a suitable selection of material, it is possible to provide the extension 414 with significantly different physical characteristics from the body, notably it can be made of soft material which will have very little effect on the inner wall surface of a vein. Similarly, the strength at the shoulder can be changed by using inserts of soft material or even providing plugs rather than inserts in the manner described with reference to FIG. 3.

Structures such as shown in FIGS. 3, 13, and 19 are exemplary of tips which are tapered. Some are frustroconical whereas others tend to have a shoulder such as that shown in FIG. 19. However, functionally they are all tapered since they will dilate tissue as they are moved along a Seldinger wire into position in a patient. For this reason, in the terminology of this application, the word "tapered" is intended to include any structure at the end which is capable of such dilation.

It will be appreciated that various other modifications may be made to the catheter, and to the processes for making parts of the catheter as described, without departing from the scope of the invention, for example, the material used to form the tube and inserts may be any suitable medical grade thermoplastic. Also, the positioning of the apertures and the number of apertures is to some extent a matter of choice. Also the length of the conical tip can be varied to include apertures in the wall of the tip. While such a structure is more complicated to make, the flow pattern would be advantageous.

Although the catheter has been described in use in haemodialysis in a subclavian vein, it would also be appreciated that it can be used in both femoral and jugular veins, and can also be used in other blood treatments including apheresis, haemoperfusion and non-blood related treatments involving nutrition and drug therapies.

What is claimed is:

1. A triple lumen catheter comprising:
   a. an outer tube having a proximal end and a distal end;
   b. an inner tube having a proximal end and a distal end and defining therewithin a first lumen, said inner tube having an outer diameter less than the inner diameter of said outer tube, said inner tube being disposed within said outer tube to define an interior space between the outside of said inner tube and the inside of said outer tube;
   c. a first septum extending from a first point on the outside of said inner tube to a first point on the inside of said outer tube;
   d. a second septum extending between a second point on said outside of said inner tube and a second point on said inside of said outer tube, said first septum and said second septum thereby separating said interior space into a second lumen located on one side of said first septum, said inner tube, and said second septum, and a third lumen located on the opposite side of said first septum, said inner tube, and said second septum;
   e. a frustoconical distal tip section at said distal end of said outer tube enclosing said distal end of said inner tube, the outer wall of said distal tip section tapering radially inwardly from said distal end of said outer tube into engagement with said inner tube at said distal end thereof, said outer wall of said distal tip section terminating at said distal end of said inner tube and thereat defining an open apex of said distal tip section through which said first lumen communicates with the exterior of said distal tip section; and
   f. plural openings formed through said outer tube at said distal end thereof, each of said second lumen and said third lumen communicating with the exterior of said outer tube through respective of said openings.

2. A catheter as recited in claim 1, wherein:
   a. the extent of said first septum measured normal to said width thereof defines the thickness of said first septum;
   b. the extent of said second septum measured perpendicular to said width thereof defines the thickness of said second septum; and
   c. said thickness of said first septum is equal to said thickness of said second septum.

3. A catheter as recited in claim 2, wherein said thickness of said first septum and said thickness of said second septum are each about 0.010 inches.

4. A catheter as recited in claim 2, wherein:
   a. said thickness of said first septum is equal to the thickness of the wall of said inner tube; and
   b. said thickness of said second septum is equal to the thickness of the wall of said inner tube.

5. A catheter as recited in claim 2, wherein:
   a. said thickness of said first septum is less than the thickness of the wall of said outer tube; and
   b. said thickness of said second septum is less than said thickness of said outer tube.

6. A catheter as recited in claim 1, wherein the thickness of the wall of said outer tube is greater than the thickness of the wall of said inner tube.

7. A catheter as recited in claim 6, wherein:
   a. said thickness of said wall of said outer tube is about 0.013 inches; and
   b. said thickness of said wall of said inner tube is about 0.01 inches.

8. A catheter as recited in claim 1, wherein:
   a. the lateral extent of said first septum measured between said first point on said outside of said inner tube and said first point on said inside of said outer tube defines the width of said first septum;
   b. the lateral extent of said second septum between said second point on said outside of said inner tube and said second point on said inside of said outer tube defines the width of said second septum, and
   c. said width of said first septum is substantially equal to said width of said second septum.

9. A catheter as recited in claim 1, wherein said first septum and said second septum are coplanar.

10. A catheter as recited in claim 1, wherein the area of the transverse cross section of said second lumen is about 0.0048 square inches.

11. A catheter as recited in claim 1, wherein the area of the transverse cross section of said second lumen is equal to the area of the transverse cross section of said third lumen.

12. A catheter as recited in claim 1, wherein said outer tube, said inner tube, said first septum, and said second septum are integrally interconnected.

13. A catheter as recited in claim 1, wherein the inner diameter of said inner tube is about 0.04 inches.

14. A catheter as recited in claim 1, wherein the outer diameter of said outer tube is about 0.149 inches.

15. A triple lumen catheter comprising:
   a. a catheter body comprising:
      i. an outer tube having a proximal end and a distal end;
      ii. an inner tube having a proximal end and a distal end and defining therewithin a first lumen, said inner tube having an outer diameter less than the inner diameter of said outer tube, said inner tube being disposed within said outer tube to define an interior space between the outside of said inner tube and the inside of said outer tube;

iii. a first septum extending from a first point on the outside of said inner tube to a first point on the inside of said outer tube;

iv. a second septum extending between a second point on said outside of said inner tube and a second point on said inside of said outer tube, said first septum and said second septum thereby separating said interior space into a second lumen located on one side of said first septum, said inner tube, and said second septum, and a third lumen located on the opposite side of said first septum, said inner tube, and said second septum;

b. a frustoconical distal tip section at said distal end of said outer tube enclosing said distal end of said inner tube, the outer wall of said distal tip section tapering radially inwardly from said distal end of said outer tube into engagement with said inner tube at said distal end thereof, said outer wall of said distal tip section terminating at said distal end of said inner tube and thereat defining an open apex of said distal tip section through which said first lumen communicates with the exterior of said distal tip section; and c. access means attached to said proximal end of said outer tube and said proximal end of said inner tube for affording fluid communication individually with said first lumen, said second lumen, and said third lumen.

16. A catheter as recited in claim 15, wherein each of said second lumen and said third lumen have a C-shaped transverse cross section.

17. A catheter as recited in claim 15, wherein the transverse cross section of said second lumen is congruent to the transverse cross section of said third lumen.

18. A catheter as recited in claim 15, wherein said access means comprises:

a. a connector attached to said proximal end of said outer tube and said proximal end of said inner tube;

b. a first access tube attached to said connector and communicating therethrough with said first lumen;

c. a second access tube attached to said connector and communicating therethrough with said second lumen; and d. a third access tube attached to said connector and communicating therethrough with said third lumen.

* * * * *

(12) EX PARTE REEXAMINATION CERTIFICATE (5503rd)
United States Patent
Martin et al.

(10) Number: US 6,206,849 C1
(45) Certificate Issued: *Sep. 12, 2006

(54) MULTIPLE LUMEN CATHETER

(75) Inventors: Geoffrey S. Martin, Mississauga (CA); Michael R. Leblanc, Mississauga (CA)

(73) Assignee: Vas-Cath Incorporated, Mississauga (CA)

Reexamination Request:
No. 90/007,116, Jul. 13, 2004

Reexamination Certificate for:
Patent No.: 6,206,849
Issued: Mar. 27, 2001
Appl. No.: 09/139,705
Filed: Aug. 25, 1998

( * ) Notice: This patent is subject to a terminal disclaimer.

(Under 37 CFR 1.47)

Related U.S. Application Data

(63) Continuation of application No. 08/481,169, filed on Jun. 7, 1995, now Pat. No. 5,797,869, which is a continuation of application No. 08/205,331, filed on Mar. 3, 1994, now Pat. No. 5,472,417, which is a continuation of application No. 07/785,351, filed on Oct. 30, 1991, now abandoned, which is a continuation of application No. 07/288,364, filed on Dec. 27, 1988, now Pat. No. 5,195,962.

(30) Foreign Application Priority Data

Dec. 22, 1987 (CA) ............................................. 555076

(51) Int. Cl.
*A63M 3/00* (2006.01)

(52) U.S. Cl. .......................... 604/43; 604/264; 604/523
(58) Field of Classification Search ................... 604/43, 604/117, 264, 523, 535
See application file for complete search history.

(56) References Cited

U.S. PATENT DOCUMENTS

| 256,590 A | 4/1882 | Pfarre |
|---|---|---|
| 701,075 A | 5/1902 | McCully |
| 1,060,665 A | 5/1913 | Bell |
| 1,596,754 A | 8/1926 | Moschelle |
| 3,319,628 A | 5/1967 | Halligan ..................... 128/276 |
| 3,430,631 A | 3/1969 | Abramson ................... 128/350 |

(Continued)

FOREIGN PATENT DOCUMENTS

| CA | 1216205 | 1/1987 |
|---|---|---|
| CA | 1225299 | 8/1987 |

(Continued)

OTHER PUBLICATIONS

Shaldon, Stanley, et al., "Haemodialysis by Percutaneous Catheterization of the Femoral Artery and Vein With Regional Heparinisation," LANCET 857–59 (Oct. 14, 1961).

(Continued)

*Primary Examiner*—Michael O'Neill

(57) ABSTRACT

The invention provides a cylindrical elongate body extending from a proximal to a distal end, the body defining two similar longitudinally extending lumens separated by a septum and a further lumen defined within the septum, a tip extending from the distal end of the body defining a part of the further lumen, a connector at the proximal end, tubes coupled to the connector and in fluid communication through the connector one with each of the respective lumens, the body defining openings providing access one to each of the longitudinally extending lumens, the openings being spaced from one another longitudinally of the body and the further lumen extending longitudinally beyond the longitudinally extending lumens and through the tip, the further lumen terminating at an opening at the distal end of the tip and the tip being convergently tapered as it extends longitudinally from the body and the longitudinally extending lumens being blocked immediately adjacent and distally of the openings.

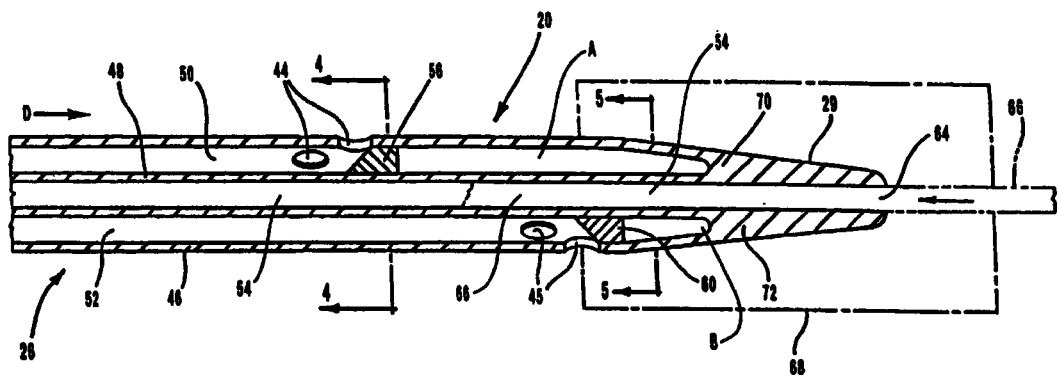

U.S. PATENT DOCUMENTS

| | | | |
|---|---|---|---|
| 3,752,510 A | 8/1973 | Windischman et al. | 285/334.4 |
| 4,000,739 A | 1/1977 | Stevens | 128/214.4 |
| 4,014,333 A | 3/1977 | McIntyre | 128/240 |
| 4,291,691 A | 9/1981 | Cabal et al. | 128/204.18 |
| 4,323,065 A | 4/1982 | Kling | 128/214 R |
| 4,563,181 A | 1/1986 | Wijayarathna et al. | 604/280 |
| 4,596,564 A | 6/1986 | Spetzler et al. | 604/281 |
| 4,717,379 A | 1/1988 | Ekholmer | 604/43 |
| 6,206,849 B1 | 3/2001 | Martin et al. | 604/43 |

FOREIGN PATENT DOCUMENTS

| | | | |
|---|---|---|---|
| CA | 1330285 | 6/1994 | 128/93 |
| DE | 3853058 | 7/1995 | |
| EP | 117093 A2 | 8/1984 | |
| EP | 117093 B1 | 4/1988 | |
| EP | 322225 A2 | 6/1989 | |
| EP | 322225 A3 | 5/1991 | |
| EP | 322225 B1 | 2/1995 | |
| ES | 529011 | 10/1984 | |
| FR | 322225 | 3/1995 | |
| IT | 322225 | 4/1995 | |
| JP | 59-156353 | 9/1984 | |
| JP | 2832722 | 10/1998 | |
| ZA | 84/1197 | 9/1984 | |

OTHER PUBLICATIONS

Shaldon, Stanley, et al., "Refrigerated Femoral Venous—Venous Haemodialysis With Coil Preservation for Rehabilitation of Terminal Uraemic Patients," Brit. Med. J. 1716–17 (Jun. 29, 1963).

Seldinger, Sven Ivar, "Catheter Replacement of the Needle in Percutaneous Arteriography," presentation at Congress of Northern Association of Medical Radiology, Helsinki; (Jun. 1952), published in 39 Acta Radiologia 368–76 (1953).

Uldal, P.R. et al., "A Subclavian Cannula for Temporary Vascular Access for Hemodialysis of Plasmapheresis," presented at Clinical Dialysis and Transport Forum, New Orleans (Nov. 1978) published in 8 Dialysis & Transplantation 963–68 (Oct. 1979).

Communication Pursuant to Article 96(2) and Rule 51(2) EPC (Examination Report) dated Jul. 23, 1993, in prosecution of European Patent No. 322,225.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

* * * * *